United States Patent

Shieh et al.

[11] Patent Number: 5,841,914
[45] Date of Patent: Nov. 24, 1998

[54] MOLECULAR DETECTION APPARATUS AND METHOD USING OPTICAL WAVEGUIDE DETECTION

[75] Inventors: Chan-Long Shieh, Paradise Valley, Ariz.; Donald E. Ackley, Lambertville, N.J.; George N. Maracas, Phoenix; Thomas B. Harvey, III, Scottsdale, both of Ariz.

[73] Assignee: Motorola, Inc., Schaumburg, Ill.

[21] Appl. No.: 861,927

[22] Filed: May 22, 1997

Related U.S. Application Data

[63] Continuation of Ser. No. 634,103, Apr. 17, 1996, Pat. No. 5,671,303.

[51] Int. Cl.[6] .............................. G02B 6/00; G01N 21/41
[52] U.S. Cl. .......................... 385/12; 385/129; 385/130; 385/131; 385/14; 385/147; 356/128
[58] Field of Search .............................. 385/12, 129, 130, 385/131, 132, 14, 37, 147; 356/128, 136, 328, 345, 351

[56] References Cited

U.S. PATENT DOCUMENTS

| | | |
|---|---|---|
| 4,815,843 | 3/1989 | Tiefenthaler et al. ................. 356/128 |
| 5,120,131 | 6/1992 | Lukosz .................................. 356/351 |
| 5,194,393 | 3/1993 | Hugl et al. ............................. 436/525 |
| 5,344,784 | 9/1994 | Attridge ................................ 436/518 |
| 5,439,647 | 8/1995 | Saini .................................... 385/50 X |
| 5,455,178 | 10/1995 | Fattinger .............................. 436/164 |
| 5,479,260 | 12/1995 | Fattinger .............................. 356/361 |
| 5,492,840 | 2/1996 | Malmqvist et al. ................... 436/518 |
| 5,671,303 | 9/1997 | Shieh et al. ............................. 385/12 |

*Primary Examiner*—Brian Healy
*Attorney, Agent, or Firm*—James E. Gauger; Douglas D. Fekete

[57] ABSTRACT

A target molecule at a binding site is detected using an optical waveguide having a surface proximate to the binding site, and a waveguide detector coupled to the optical waveguide. An incident light beam is applied to the binding site along an axis transverse to the surface of the optical waveguide. The incident light beam impinges an optical indicator associated with the target molecule to form secondary light which is coupled into the optical waveguide. The secondary light is detected by the waveguide detector to thereby detect the target molecule.

10 Claims, 5 Drawing Sheets

MOLECULAR DETECTION APPARATUS AND METHOD USING OPTICAL WAVEGUIDE DETECTION

This is a continuation of application Ser. No. 08/634,103, filed on Apr. 17, 1996, now U.S. Pat. No. 5,671,303.

FIELD OF THE INVENTION

The present invention relates to methods and systems for molecular detection using optical waveguides.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

Various approaches have been utilized to detect a hybridization event at a binding site. In one approach, a radioactive marker is attached to each of a plurality of molecules in the sample. The binding of a molecule to a molecular receptor is then detectable by detecting the radioactive marker.

Other approaches for detection utilize fluorescent labels, such as fluorophores which selectively illuminate when hybridization occurs. These fluorophores are illuminated by a pump light source external to the substrate. An external charge-coupled device (CCD) camera is utilized to detect fluorescence from the illuminated fluorophores.

An optical-detection-based DNA chip is disclosed in "Real-Time Detection of DNA Hybridization and Melting on Oligonucleotide Arrays by using Optical Wave Guides", Proceedings of the National Academy of Sciences, Vol 92, pp. 6379–6383. The DNA chip described in this article utilizes a glass substrate having a surface which defines the binding sites. The glass substrate has an end adjacent to the surface into which light is injected by an external light source. An external CCD camera is utilized to detect scatter light at the binding sites at which hybridization occurs.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Embodiments of the present invention advantageously provide a molecular detection apparatus that incorporates binding sites and optical detectors onto a single chip. The detectability of binding events is improved by only allowing propagation of secondary light (such as scatter light or fluorescent light) into an optical waveguide on the chip. Incident light is applied along an axis transverse to a surface of the optical waveguide in order to be substantially uncoupled into the optical waveguide.

Figure 1:
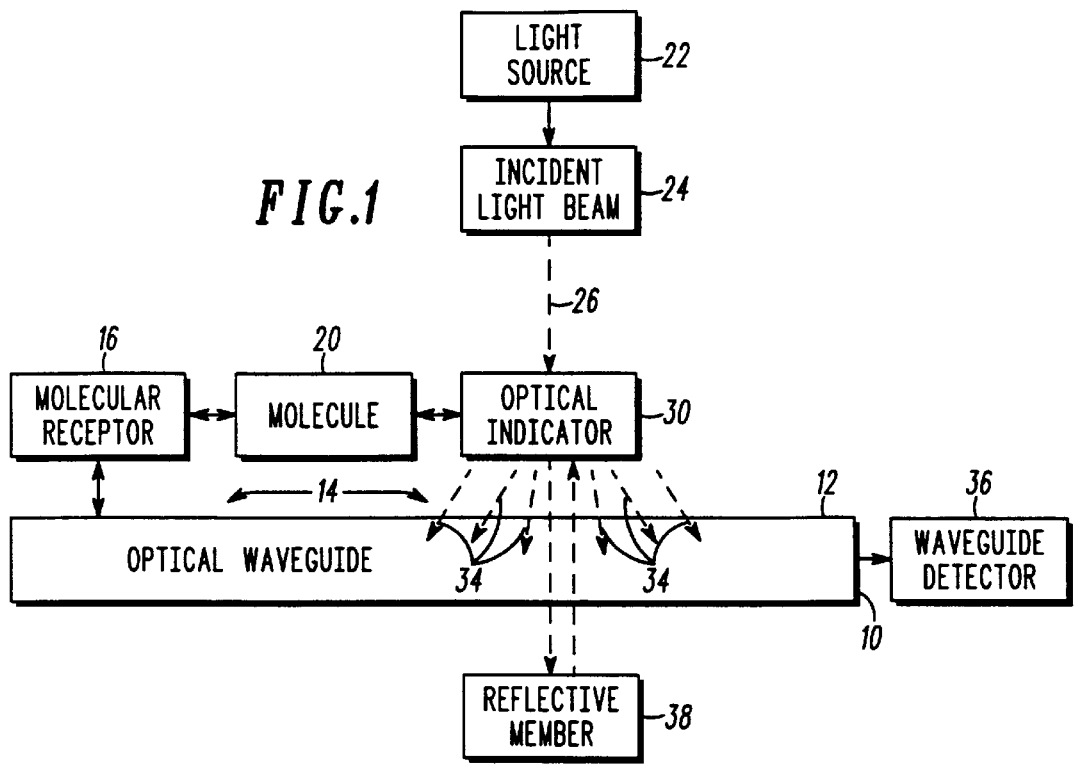
FIG. 1 is a block diagram of an embodiment of a molecular detection apparatus in accordance with the present invention.

FIG. 1 is a block diagram of an embodiment of a molecular detection apparatus in accordance with the present invention. The molecular detection apparatus comprises an optical waveguide 10 having a surface 12 which defines a binding site 14. Typically, the binding site 14 is utilized to receive a molecular receptor 16 having a specific affinity to a target molecule 20 which is to be detected. For example, the molecular receptor 16 can include a chain of at least one nucleotide which hybridizes with a complementary chain of at least one nucleotide included in the target molecule 20. Here, the molecular receptor 16 can include a DNA probe for detecting a complementary DNA sequence in the target molecule 20. It is noted, however, that the scope of the present invention is not limited to sensing the hybridization of DNA molecules. For example, embodiments of the present invention may be utilized to detect antibody-antigen binding.

A light source 22 applies an incident light beam 24 to the binding site 14. The incident light beam 24 is directed along an axis 26 transverse to the surface 12 of the optical waveguide 10. Preferably, the axis 26 is substantially normal to the surface 12 so that the incident light beam 24 is not directly coupled into the optical waveguide 10. The incident light beam 24 can have the form of a collimated light beam or a pump light beam, for example.

The incident light beam 24 impinges an optical indicator 30 bound at the binding site 14. The optical indicator 30 is indicative of a binding event between the target molecule 20 and the molecular receptor 16. The optical indicator 30 can include at least one fluorescent molecule. Alternatively, the optical indicator 30 can include at least one scattering member which scatters the incident light beam 24. Here, the optical indicator 30 can have the form of a scattering bead attached to the target molecule 20.

Secondary light 34 is formed when the incident light beam 24 impinges the optical indicator 30. For a fluorescent indicator, the secondary light 34 includes fluorescent light which emanates from the optical indicator 30. For a scattering indicator, the secondary light 34 includes scatter light from the optical indicator 30.

Regardless of its form, a portion of the secondary light 34 is coupled into the optical waveguide 10. Since the propagating field in the optical waveguide 10 travels parallel to the surface 12, the incident light beam 24 is substantially uncoupled into the optical waveguide 10. Hence, only those fluorescent events or scattering events that occur at the surface 12 efficiently couple into the optical waveguide 10.

The secondary light 34 propagates through the optical waveguide 10 in a direction transverse to the axis 26. A waveguide detector 36 is coupled to the optical waveguide 10 to detect the secondary light 34. By detecting the secondary light 34, the molecular detection apparatus detects the binding event between the target molecule 20 and the molecular receptor 16.

To enhance the differentiation of fluorescent events, the optical waveguide 10 can be made of a material which absorbs the incident light beam 24 but does not absorb the secondary light 34. Here, any stray portion of the incident light beam 24 which couples into the optical waveguide 10 is attenuated before reaching the waveguide detector 36. The differentiation of fluorescent events can be further enhanced by increasing the number of fluorescent molecules attached on the surface 12. This can be achieved by attaching multiple fluorescent dye molecules to a bead which is attached to the target molecule 20.

Optionally, a reflective member 38 is included to reflect a portion of the incident light beam 24 passing through the binding site 14 back toward the binding site 14. The reflective member 38 is beneficial for enhancing an illumination of the binding site 14 without having to increase an intensity of the incident light beam 24.

Figure 2:
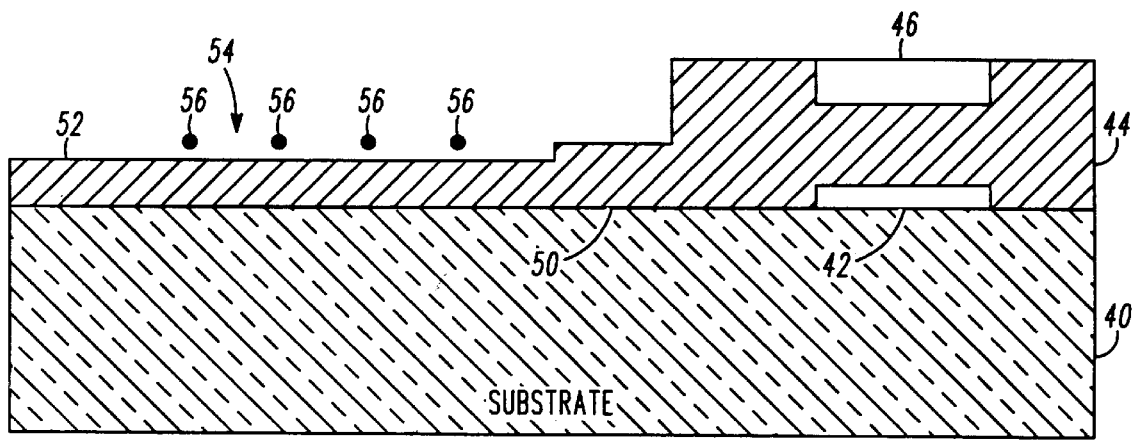
FIG. 2 is a schematic, cross-sectional view of another embodiment of the molecular detection apparatus.

FIG. 2 is a schematic, cross-sectional view of another embodiment of the molecular detection apparatus. The molecular detection apparatus is fabricated on a substrate 40. The substrate 40 is preferably formed by a smooth substrate member such as a Si wafer or glass. An ohmic contact 42 is disposed on the substrate 40. The ohmic contact 42 can be formed by a layer of metal, such as Cr, deposited on the substrate 40.

Disposed on the ohmic contact 42 is a photodetector 44. In a preferred embodiment, the photodetector 44 is formed by an a-Si PIN diode deposited on the ohmic contact 42. The ohmic contact 42 provides an n-contact for the PIN diode. A second ohmic layer 46 is disposed on the photodetector 44. The second ohmic layer 46 is deposited on the a-Si PIN diode to provide a p-contact. The resulting structure can then be patterned into one or more individual detector diodes.

An optical waveguide 50 is disposed adjacent to the photodetector 44 on the substrate 40. The optical waveguide 50 can be formed of a dielectric material, such as SiN, deposited on the substrate 40. For fluorescent detection, the optical waveguide 50 is formed by an a-SiC material of an appropriate composition to absorb an incident light beam, but transmit fluorescent light.

The optical waveguide 50 has a top surface 52 which defines a binding site 54. The binding site 54 receives an incident light beam along an axis transverse to the top surface 52. Secondary light is generated when the incident light beam impinges an optical indicator 56 indicative of a binding event. The secondary light is coupled into the optical waveguide 50 and communicated to the photodetector 44. The binding event is then detected by a signal generated between the ohmic contact 42 and the second ohmic contact 46.

Figure 3:
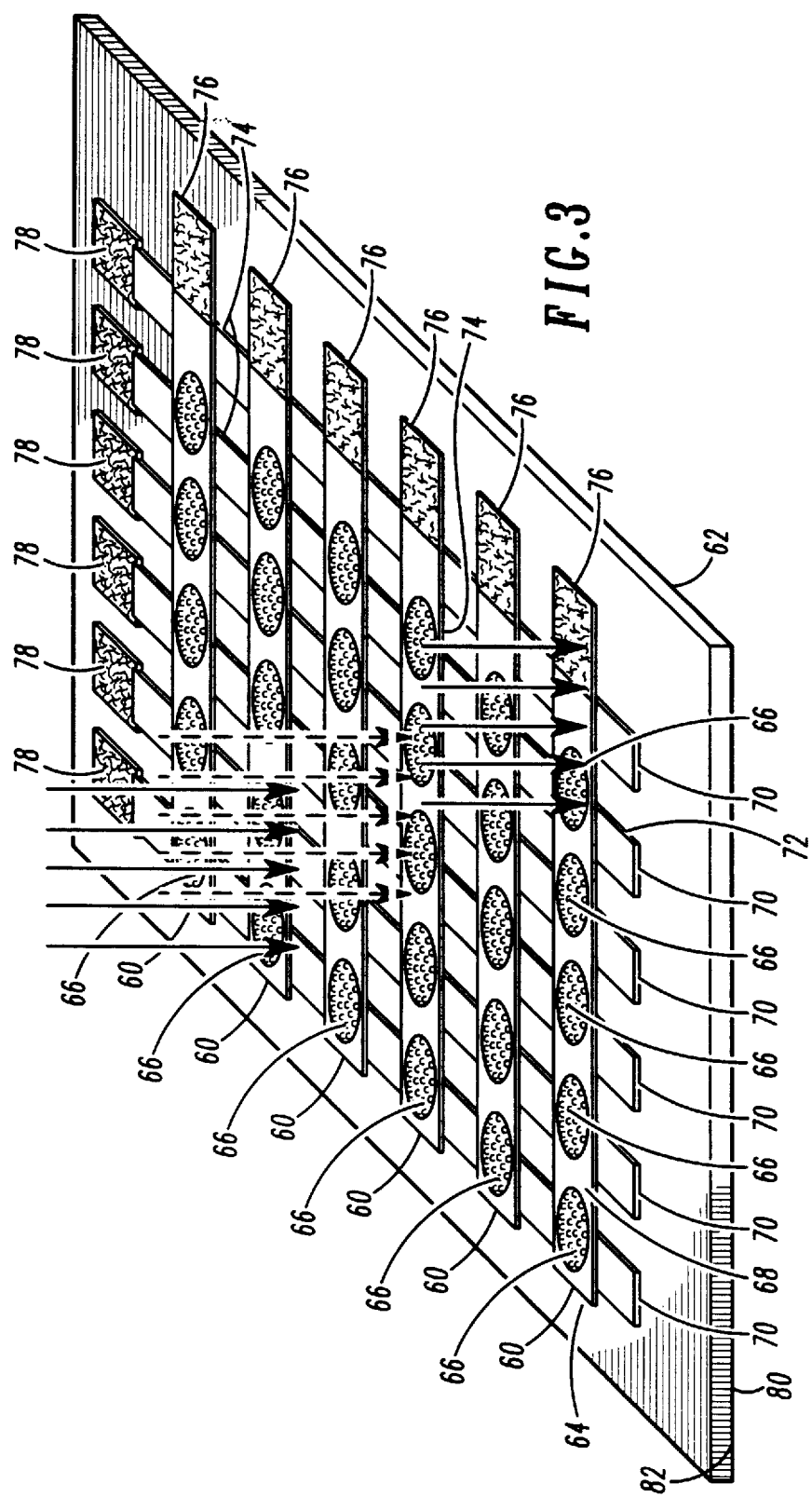
FIG. 3 is an illustration of an embodiment of a molecular detection array in accordance with the present invention.

FIG. 3 is an illustration of an embodiment of a molecular detection array in accordance with the present invention. The molecular detection array defines a plurality of binding sites arranged as an array. In practice, each of the plurality of binding sites receives a respective molecular receptor for detecting a corresponding target molecule. Each of the binding sites is illuminated by a pump beam to generate secondary light, such as fluorescent light or scatter light, when an optical indicator is present.

The molecular detection array includes a first plurality of optical waveguides 60 supported by a substrate 62. Each of the first plurality of optical waveguides 60 has a respective subset of the binding sites in optical communication therewith. This is illustrated representatively by a first optical waveguide 64 having binding sites 66 defined on a surface 68.

A second plurality of optical waveguides 70 is also supported on the substrate 62. Each of the second plurality of optical waveguides 70 has a respective subset of the binding sites in optical communication therewith. This is illustrated representatively by a second optical waveguide 72 having binding sites 74 proximate thereto.

In one embodiment, the first plurality of optical waveguides 60 is located above the second plurality of optical waveguides 70 on the molecular detection array. Here, the first plurality of optical waveguides 60 and the second plurality of optical waveguides 70 each has a planar surface oriented transverse, and preferably normal, to an axis of the pump beam. As a result, the pump beam is substantially uncoupled into the first plurality of optical waveguides 60 and the second plurality of optical waveguides 70.

In another embodiment, the first plurality of optical waveguides 60 and the second plurality of optical waveguides 70 are located on a single plane. Here, the first plurality of optical waveguides 60 and the second plurality of optical waveguides 70 intersect on the single plane in proximity to each of the plurality of binding sites. Each resulting intersection region has a planar surface oriented transverse, and preferably normal, to an axis of the pump beam so that the pump beam is substantially uncoupled therein.

The first plurality of optical waveguides 60 and the second plurality of optical waveguides 70 are arranged so that each of the plurality of binding sites is in optical proximity to one of the first plurality of waveguides 60 and one of the second plurality of optical waveguides 70. As illustrated, this can be achieved by arranging the first plurality of optical waveguides 60 so that each is proximate to a respective row of the binding sites, and by arranging the second plurality of optical waveguides 70 so that each is proximate to a respective column of the binding sites. As a result, secondary light generated at a binding site is isotropically coupled into the planes of two optical waveguides below the binding site: one from the first plurality of optical waveguides 60 and one from the second plurality of optical waveguides 70.

The molecular detection array further includes a first plurality of detectors 76 and a second plurality of detectors 78 supported by the substrate 62. Each of the first plurality of detectors 76 is coupled to a respective one of the first plurality of optical waveguides 60. Similarly, each of the second plurality of detectors 78 is coupled to a respective one of the second plurality of optical waveguides 70. Using this configuration, secondary light generated at a binding site is detected by two detectors: one from the first plurality of detectors 76 and one from the second plurality of detectors 78. By reading out a detected signal from each combination of detectors, binding sites with matching targets can be readily identified.

The sensitivity of detection in this embodiment can be doubled by utilizing a high reflectivity coating 80 on a back side 82 of the substrate 62. The high reflectivity coating 80 acts to reflect a pump beam which illuminates the binding sites back through the binding sites for a second pass.

Figure 4:
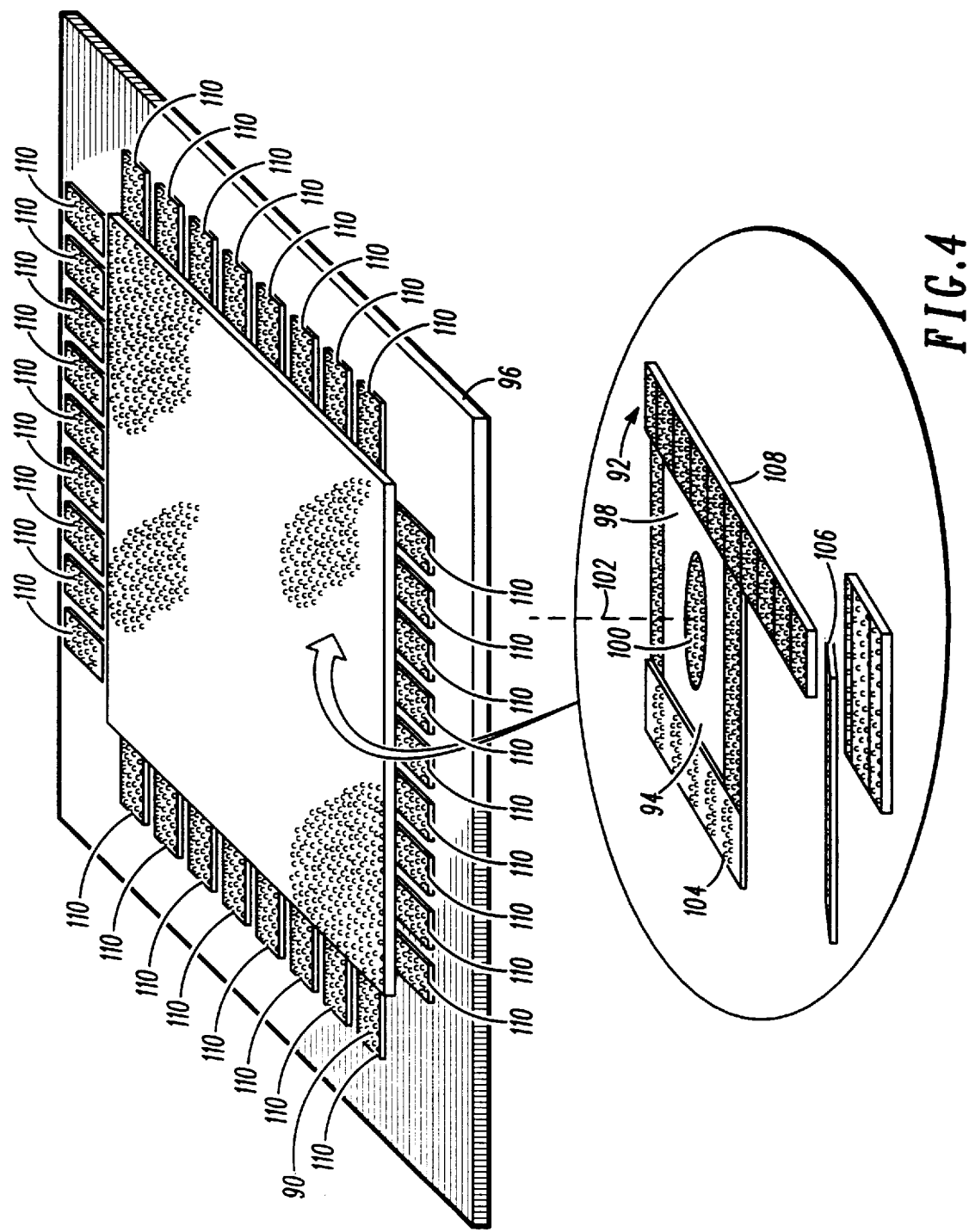
FIG. 4 is an illustration of another embodiment of a molecular detection array in accordance with the present invention.

FIG. 4 is an illustration of another embodiment of a molecular detection array in accordance with the present invention. The molecular detection array defines a plurality of binding sites 90 which can be arranged as an array. In this embodiment, each of the plurality of binding sites 90 has its own optical waveguide and waveguide detector. A representative one of the plurality of binding sites, indicated by reference numeral 92, is illustrated in detail.

An optical waveguide 94 is located proximate to the binding site 92. The optical waveguide 94 is supported by a substrate 96. The optical waveguide 94 has a surface 98 to which one or more molecular receptors 100 are attached. The surface 98 is oriented transverse to an axis 102 along which a pump beam is directed to illuminate the binding site 92.

A waveguide detector 104 is coupled to the optical waveguide 94 to detect secondary light coupled therein. The waveguide detector 104 can be embodied by a photodiode or other like photodetector fabricated on the substrate 96 as described earlier. Preferably, the waveguide detector 104 is shaped to substantially surround the optical waveguide 94 at the binding site 92. The waveguide detector 104 can have either a rectangular shape or a circular shape, for example, to surround the binding site 92. By surrounding the binding site 92 with the waveguide detector 104, all of the secondary light coupled into the optical waveguide 94 is collected by the waveguide detector 104. This configuration is useful in minimizing optical cross-talk between adjacent waveguides.

A read-out device 106 is coupled to the waveguide detector 104 to allow matrix addressing of the binding site 92. The read-out device 106 can take the form of a thin-film transistor which is coupled to the waveguide detector 104 by an interconnect 108. The read-out device 106 is addressed via a plurality of electrical contacts 110 using standard matrix addressing techniques used in active matrix displays.

Figure 5:
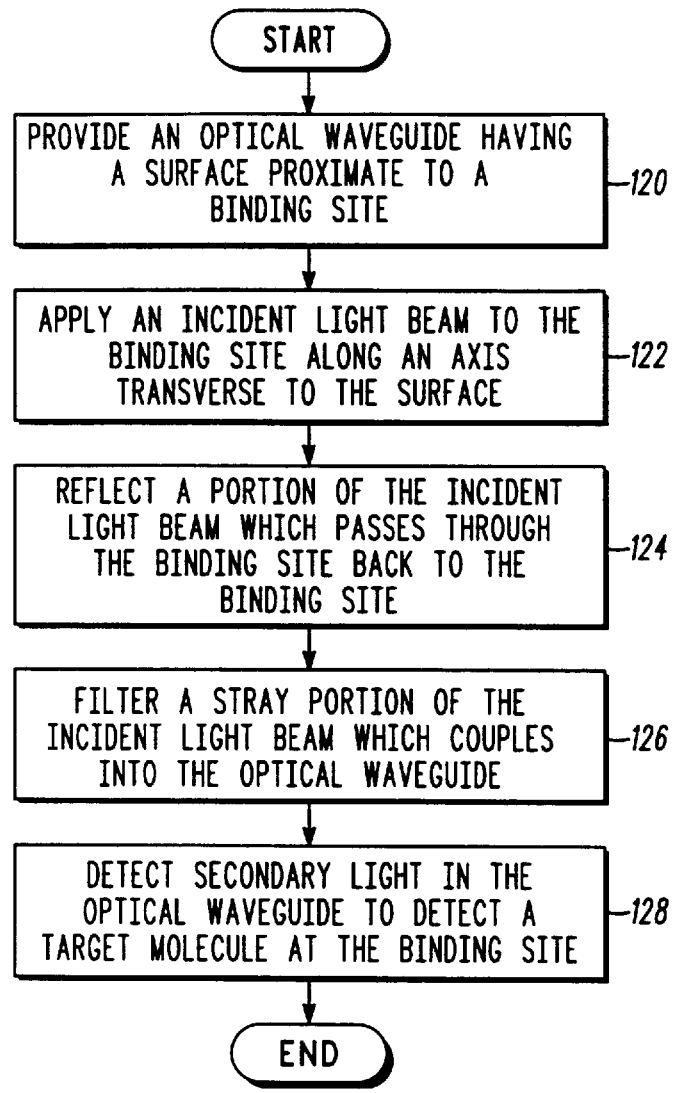
FIG. 5 is a flow chart of an embodiment of a method of molecular detection in accordance with the present invention.

FIG. 5 is a flow chart of an embodiment of a method of molecular detection in accordance with the present invention. As indicated by block 120, the method includes a step of providing an optical waveguide having a surface proximate to a binding site. Preferably, the optical waveguide is provided within an embodiment of a molecular detection apparatus as described herein, although the steps described in this method should not be construed as being limited to the described embodiments.

As indicated by block 122, a step of applying an incident light beam to the binding site is performed. The incident light beam is applied along an axis transverse to the surface of the optical waveguide. Preferably, the incident light beam is applied along an axis normal to the surface. The incident light beam impinges an optical indicator bound at the binding site to form secondary light which is coupled into the optical waveguide.

Optionally, a step of reflecting a portion of the incident light beam which passes through the binding site back to the binding site is performed, as indicated by block 124. This step is beneficial for enhancing an illumination of the binding site.

As indicated by block 126, an optional step of filtering a stray portion of the incident light beam which couples into the optical waveguide is performed. As described earlier, the stray portion of the incident light beam can be filtered by utilizing a waveguide material which absorbs the incident light while transmitting the secondary light.

As indicated by block 128, a step of detecting the secondary light in the optical waveguide is performed to detect a target molecule at the binding site. Preferably, this step includes detecting a signal generated from a waveguide detector coupled to and integrated with the optical waveguide on a substrate. The signal is indicative of an amount of secondary light detected. Here, the target molecule is detected if the signal is beyond a predetermined threshold.

Figure 6:
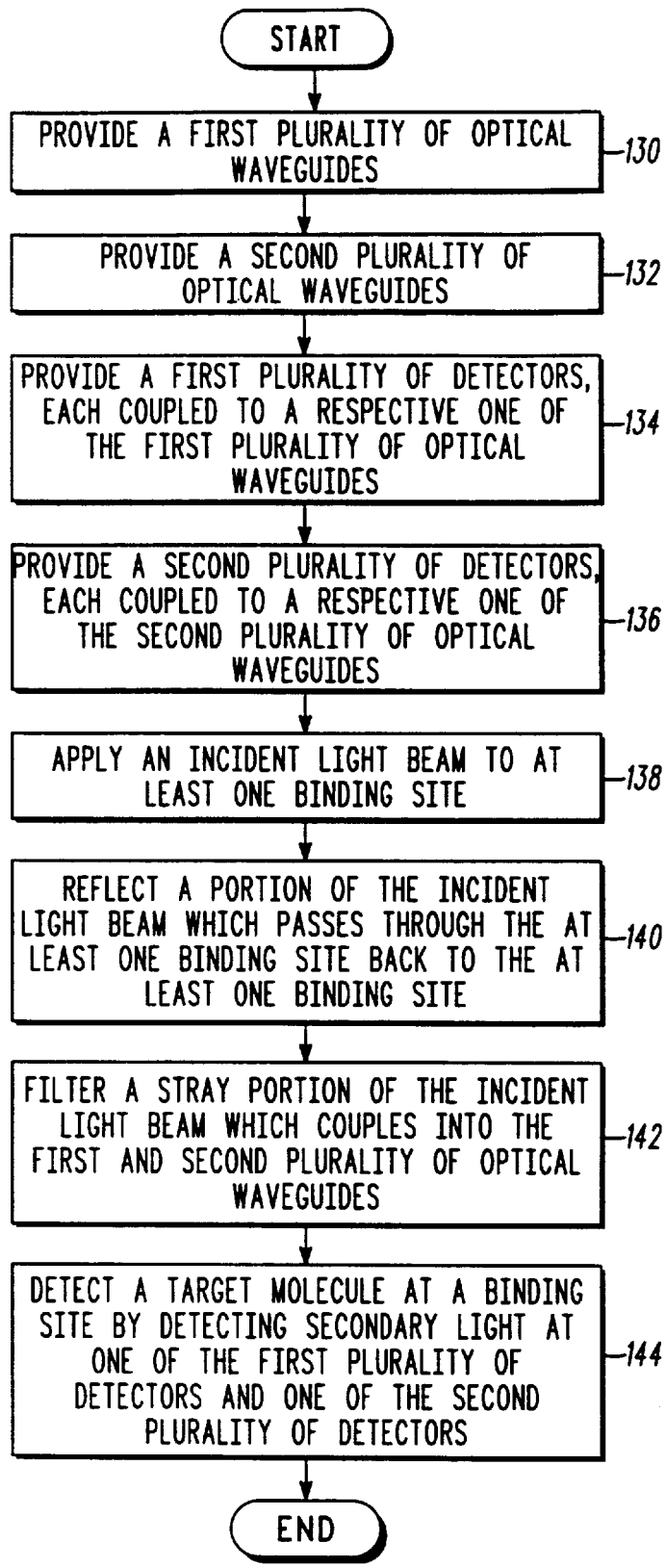
FIG. 6 is a flow chart of another embodiment of a method of molecular detection in accordance with the present invention.

FIG. 6 is a flow chart of another embodiment of a method of molecular detection in accordance with the present invention. As indicated by block 130, a step of providing a first plurality of optical waveguides is performed. Each of the first plurality of optical waveguides has a respective subset of a plurality of binding sites in optical communication therewith. As indicated by block 132, a step of providing a second plurality of optical waveguides is performed. Each of the second plurality of optical waveguides has a respective subset of the plurality of binding sites in optical communication therewith. Hence, each of the plurality of binding sites optically communicates with a respective one of the first plurality of optical waveguides and a respective one of the second plurality of optical waveguides.

As indicated by block 134, a step of providing a first plurality of detectors is performed. Each of the first plurality of detectors is coupled to a respective one of the first plurality of optical waveguides. As indicated by block 136, a step of providing a second plurality of detectors is performed. Each of the second plurality of detectors is coupled to a respective one of the second plurality of optical waveguides.

Preferably, the steps indicated by blocks 130, 132, 134, and 136 are performed by providing the molecular detection array of FIG. 3. It is noted, however, that these steps are not limited to the apparatus of FIG. 3.

As indicated by block 138, a step of applying an incident light beam to at least one binding site of the plurality of binding sites is performed. Here, for example, an incident light beam can be applied to a single binding site, to a row of the binding sites, to a column of the binding sites, or to all of the binding sites.

Optionally, a step of reflecting a portion of the incident light beam which passes through the at least one binding site back to the at least one binding site is performed, as indicated by block 140. This step is beneficial for enhancing an illumination of the at least one binding site.

Another optional step of filtering a stray portion of the incident light beam which couples into the first plurality of optical waveguides and the second plurality of optical waveguides is performed, as indicated by block 142.

As indicated by block 144, the method includes a step of detecting a target molecule at one of the plurality of binding sites by detecting secondary light at one of the first plurality of detectors and at one of the second plurality of detectors. For example, using the row-column configuration of the apparatus of FIG. 3, a target molecule is detected at a binding site by detecting secondary light at a detector corresponding to the binding site's row and a detector corresponding to the binding site's column.

Thus, there has been described herein a concept, as well as several embodiments including preferred embodiments of a molecular detection apparatus and method using optical waveguide detection.

Because the various embodiments of the present invention apply an incident light beam transverse to an axis of propagation within the optical waveguide, they provide a significant improvement in that only secondary light indicative of a binding event is coupled into the optical waveguide. As a result, the differentiation of the secondary light from the incident light beam as seen by the waveguide detector is significantly improved.

Additionally, the various embodiments of the present invention as herein-described provide matrix addressing approaches to reading binding events in an array of molecular detectors.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular detection apparatus comprising:

a substrate;

a first layer disposed on the substrate;

a photodetector disposed on the first layer, the photodetector electrically coupled to the first layer; a second layer disposed on the photodetector, the second layer electronically coupled to the photodetector; and an optical waveguide disposed adjacent the photodetector on the substrate, the optical waveguide having a surface defining a detection site.

2. The molecular detection apparatus of claim 1 wherein the photodetector includes a PIN diode, wherein the first layer provides an n-contact to the PIN diode, and wherein the second layer provides a p-contact to the PIN diode.

3. The molecular detection apparatus of claim 1 wherein the first layer and the second layer are formed of an ohmic material.

4. The molecular detection apparatus of claim 1 wherein the first layer and the second layer are formed of a metal.

5. The molecular detection apparatus of claim 1 wherein the first layer and the second layer provide a signal associated with a binding event at the detection site.

6. The molecular detection apparatus of claim 1 further comprising a molecular receptor at the detection site.

7. A molecular detection apparatus comprising:

an optical waveguide having a surface proximate to a molecular detection site; and a waveguide detector coupled to the optical waveguide, the waveguide detector shaped to substantially surround the optical waveguide at the molecular detection site.

8. The molecular detection apparatus of claim 7 further comprising a substrate which supports the optical waveguide and the waveguide detector.

9. The molecular detection apparatus of claim 7 wherein the waveguide detector has an annular shape.

10. The molecular detection apparatus of claim 7 wherein the waveguide detector has a rectangular shape.

* * * * *